United States Patent [19]

Fischer

[11] Patent Number: 4,578,055
[45] Date of Patent: Mar. 25, 1986

[54] CONTROLLED DIFFUSION MEDICAMENT APPLICATOR

[76] Inventor: Dan E. Fischer, 1345 E. 3900 South, Salt Lake City, Utah 84016

[21] Appl. No.: 604,029

[22] Filed: Apr. 26, 1984

Related U.S. Application Data

[63] Continuation of Ser. No. 60,382, Jul. 25, 1979, abandoned, which is a continuation-in-part of Ser. No. 799,168, May 23, 1977, abandoned.

[51] Int. Cl.$^4$ ............................................. A61B 10/00
[52] U.S. Cl. .......................................... 604/2; 604/3; 604/311
[58] Field of Search ..................... 604/2, 3, 310, 311; 401/134, 156, 176, 182, 185, 186, 198, 205, 209

[56] References Cited

U.S. PATENT DOCUMENTS

| 392,006 | 10/1888 | Carmichael . | |
|---|---|---|---|
| 1,438,064 | 12/1922 | Simmons . | |
| 2,170,222 | 8/1939 | Strauss | 604/2 |
| 3,519,364 | 7/1970 | Truhan | 604/2 X |
| 3,792,699 | 2/1974 | Tobin et al. | 604/2 X |
| 3,918,435 | 11/1975 | Beall et al. | 604/2 X |
| 3,924,623 | 12/1975 | Avery | 604/3 |
| 3,938,898 | 2/1976 | Reitlsnecht | 604/2 X |
| 4,225,254 | 9/1980 | Holberg et al. | 604/2 X |

OTHER PUBLICATIONS

Research Associates Newsletter, vol. 3, Issue 8, Dated Aug. 1979.
Chapter entitled "Tissue Management For Making Impressions: written by Dan E. Fischer, from the book *Restorative Techniques For Individual Teeth*, Published on or about Apr. 1981.
Advertisement for Applicant's Dento-Infusor, appearing in the Jul.-Aug. 1981 issue of Dental Products Report.
Description of use of Applicant's Dento-Infusor Device having a most recent copyright date of 1984.

*Primary Examiner*—Edward W. Coven
*Attorney, Agent, or Firm*—Workman, Nydegger & Jensen

[57] ABSTRACT

A medicament applicator having a rigid, curved delivery tube provides controlled diffusion of medicament, as well as rigidity for burnishing of tissue and removal of coagulated blood, and maneuverability for reaching desired points of application within the mouth or within an incision. The tube is curved to a pre-determined shape, and has a small amount of padding at the delivery end. Diffusion of the medicament is controlled by a pressure-applied delivery system utilizing a syringe-plunger, a syringe-capsule-plunger, a squeeze bulb or similar device. Release of the pressure-applied delivery system immediately stops the flow of medicament.

17 Claims, 6 Drawing Figures

U.S. Patent  Mar. 25, 1986  Sheet 1 of 2  4,578,055
FIG. 1
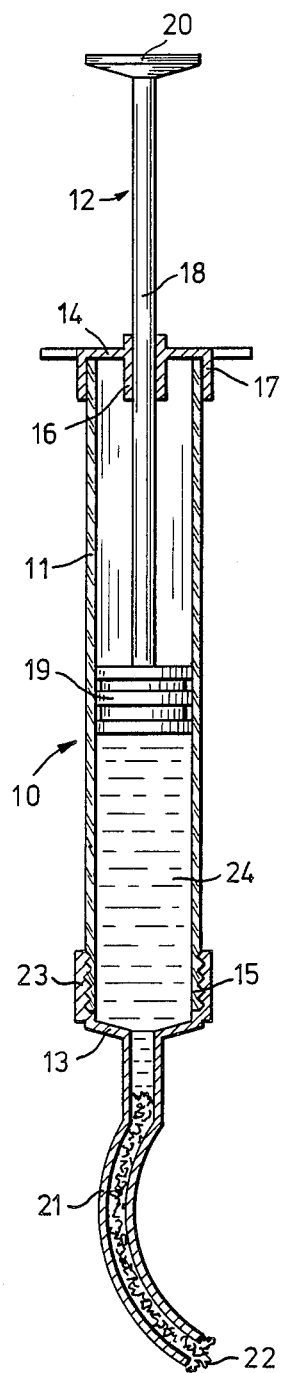
FIG. 2
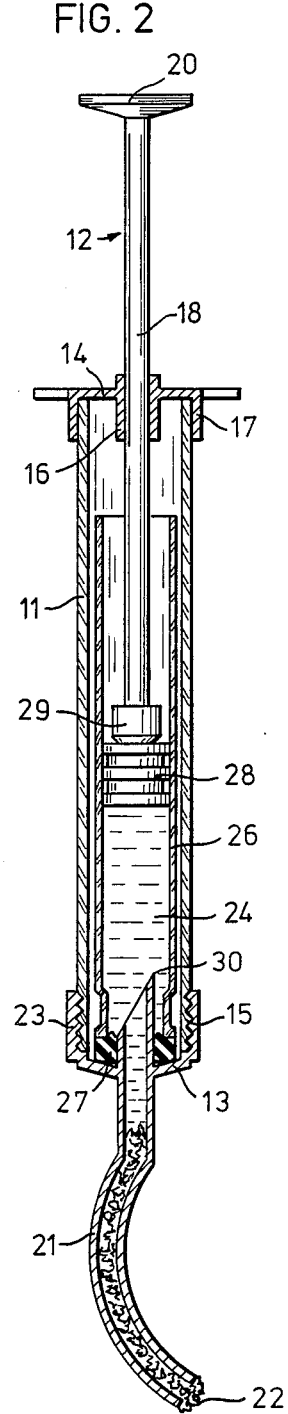
FIG. 4
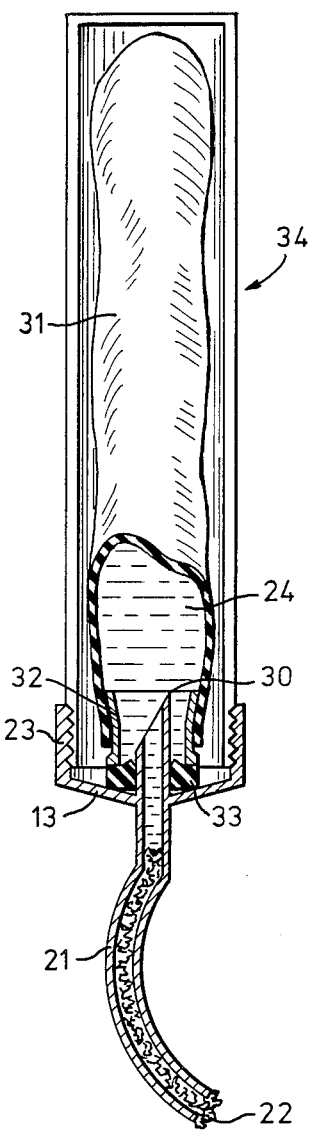
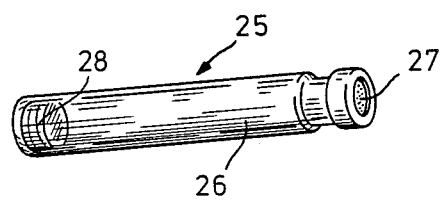
FIG. 3

CONTROLLED DIFFUSION MEDICAMENT APPLICATOR

This is a continuation of application Ser. No. 060,382, filed July 25, 1979, now abandoned, which application is a continuation-in-part application of Ser. No. 799,168, filed May 23, 1977, now abandoned.

BACKGROUND OF THE INVENTION

This invention relates to the field of fluid applicators and more specifically to medicament applicators.

Numerous devices in various forms have been developed to apply fluids to designated surfaces. The diversity of these devices range from paint brushes, quill pens, and fountain pens to felt tip pens, medicinal swabs, and power point pens. Many developments and improvements to accomplish a variety of objectives have been made. For example, in the late nineteenth century pens were developed that had internal ink reservoirs and avoided use of ink wells. Later, many devices designed to avoid leakage and terminate fluid flow to the applicator's tip were made. Applicator tips have taken a variety of forms. There are brushes, ball points, swabs, and porous textile tips to mention a few.

Despite the multitude of devices and developments, the needs of a dentist engaged in oral medicament application or a doctor engaged in delicate surgery have remained without adequate remedy. The devices that use air pressure and gravity to force capillary flow through a porous textile for a swabbing effect do not have the intricately controlled fluid flow necessary. Swab tipped devices have proved to be too large and wasteful of valuable medicaments and time. Other devices feel foreign to the dentist's or doctor's trained hand and are awkward in use.

It is an objective of the present invention to eliminate the problems recognized in the art and remedy the dentist's and doctor's needs by providing a device that is familiar in feel, can easily reach all areas within the mouth or within an incision, provides an intricate swabbing effect, and permits the dentist or doctor to control the flow of medicament in application

SUMMARY OF THE INVENTION

The medicament applicator of the invention has a syringe-type dispenser and a tube having a small amount of porous padding or filament material attached to the delivery end of the tube. The syringe type dispenser is comprised of a dispenser tube with a finger abutment cap and a plunger with a thumb disc. The tube attaches to the dispenser tube and is bent to the desired shape of a curve to accommodate access to gingival sulci, open pulp chamber, or the like, whether dental or medicinal in application. The filament or padding material protrudes slightly from the tube's end to provide a rigid swabbing effect without sharpness. This effect allows for burnishing of tissue, aids in removal of coagulated blood, and applies pressure to the tissue.

The astringent solution or other medicament is disposed within the dispenser tube. The plunger is disposed such that it slides continuously within the dispenser tube. By depressing the plunger, the medicament is forced through the tube and exudes onto the point of application. Release of the plunger creates a slight vacuum within the tube, and immediately stops the flow of medicament, thereby preventing further dispensing of medicament.

The present invention can be used in many ways with many different medicaments. It can be used to deliver astringent, hemostatic agents to a bleeding gingival sulcus prior to taking impressions, to a bleeding pulp chamber in a pulpotomy, or to a cut papilla interdentally. It can also be used to apply etching acid, such as citric or orthophosphoric acid for etching the enamel surfaces of teeth prior to resin restorations.

The present invention can be disposable or designed for office sterilization in whole or in part.

As another embodiment of the present invention, the dispenser can be designed to receive a disposable prefilled capsule containing the desired medicament.

Another embodiment of the present invention utilizes disposable squeeze bulb instead of the syringe type dispenser. With this embodiment, the flow of medicament would be controlled by squeeze pressure between the thumb and fingers when the applicator is grasped like a pen.

THE DRAWINGS

Preferred embodiments of the invention are illustrated in the accompanying drawings, in which:

FIG. 1 is a longitudinal section of the medicament applicator;

FIG. 2 is a longitudinal section of a medicament applicator adapted for capsule use with a capsule disposed therein;

FIG. 3, is a perspective view of a medicament capsule;

FIG. 4 is an elevational view of a squeeze bulb applicator;

DETAILED DESCRIPTION OF THE ILLUSTRATED EMBODIMENTS

Figure 5:
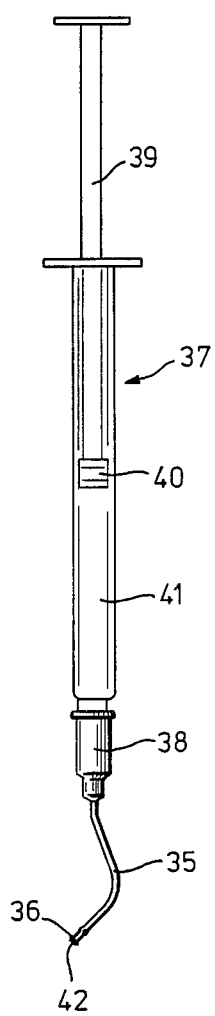
FIG. 5 is an elevational view of a preferred embodiment of the applicator.

As shown in FIG. 1, a preferred embodiment of the medicament applicator 10 is comprised of a dispenser tube 11, a plunger 12, and a detachable needle cap 13. The dispenser tube 11 is substantially cylindrical in shape, has a plunger cap 14 affixed to its lower end, and has male threads 15 grooved in its upper end or can be a Luer-Lock coupling, friction coupling or the like. It is understood that the dispenser tube 11 may be constructed with a cross section of any shape, however, circular is preferred. Said plunger cap 14 is constructed with a bore guide 16 and a finger abutment 17.

The plunger 12 is comprised of a plunger shaft 18, a stopper 19, and a thumb disc 20. Said plunger shaft 18 is disposed through the bore guide 16. Said stopper 19 has its outer edge contiguous with the inner wall of the dispenser tube 11.

The tube cap 13 has female threads 23 and a tube 21 with a preferably porous polyester cord filament 22 disposed therein. Said tube 21 is bent to any desired shape to facilitate application of a medicament 24 to difficult to reach areas within the mouth or within an incision. Said porous filament 22 protrudes slightly from the tube 21 so as to act as an intricate swab and to reduce the tube's sharpness. The filament 22 is fitted tightly enough to allow for controlled flow of medicament 24 to the tip of the tube 21. It is understood that the filament 22 may be made of any porous fiber, but polyester cord is preferred.

The dispenser tube 11 is filled with medicament 24 by removing the tube cap 13 and drawing the desired amount of said medicament 24 into said tube 11. The cap 13 is then replaced on the tube 11. By depressing the plunger 12, the medicament 24 is forced through the filament 22 and exudes onto the point of application.

The applicator 10 is constructed of easy to sterilize materials. The dispenser tube 11, plunger shaft 18, and thumb disc 20 may be constructed of glass, metal, nonporous plastic, or the like. The plunger stopper 19 may be made of a resilient rubber. The tube 21 is made of a metal so as to retain its bend and rigidity.

The medicament applicator 10 may be disposed of or office sterilized in whole or in part.

It is understood that the applicator may be designed for an air trap pump system which would deliver an even flow of medicament without constant thumb pressure after the plunger has been pumped.

Another embodiment of the present invention is illustrated in FIGS. 2 and 3. This embodiment is an adaptation for capsule use. The capsule 25 is shown in FIG. 3. Said capsule 25 is comprised of a capsule tube 26, a membrane 27, and a capsule stopper 28. The capsule 25 is shaped such that it readily fits within the dispenser tube 11. The dispenser tube 11 is the same as shown in FIG. 1. The plunger 12 is adapted to capsule use by having a rigid head 29 in place of the stopper 19. The tube cap 13 also has one adaptation, that being a sharp inner tip 30.

The capsule 25 is inserted into the dispenser tube 11. The tube cap 13 is then attached to the dispenser tube 11. By depressing the plunger 12, the capsule 25 is pushed forward until it rests again the tube cap 13 and the sharp inner tip 30 punctures the capsule membrane 27. Further pressure on the plunger 12 causes the plunger head 29 to engage and push the capsule stopper 28 forward. The capsule stopper 28 forces the medicament 24 within the capsule 25 through the filament 22. The medicament 24 exudes from the filament 22 onto the point of application.

After use, the capsule 25 may be removed from the dispenser tube 11 and disposed of.

Another embodiment of the present invention is illustrated in FIG. 4. The squeeze bulb embodiment utilizes a resilient squeeze bulb 31 instead of a syringe type delivery system. The squeeze bulb 31 is attached at its lower end to a metal cap 32 which has at its lower end a membrane 33 similar to the membrane described above in FIGS. 2 and 3. This membrane can be punctured by a sharp inner tip 30. In this manner, it may be easily squeezed between the thumb and fingers.

Before attaching the tube cap 13, the medicament 24 is poured into the squeeze bulb 31. The cap 13 is then attached. By squeezing the bulb 31 as described above, the medicament 24 is forced through the filament 22 and exudes onto the point of application.

Said squeeze bulb 31 is made of a resilient nonabsorbent, nonporous rubber. However, it is understood that any material having the above desired characteristics may be used.

Figure 6:
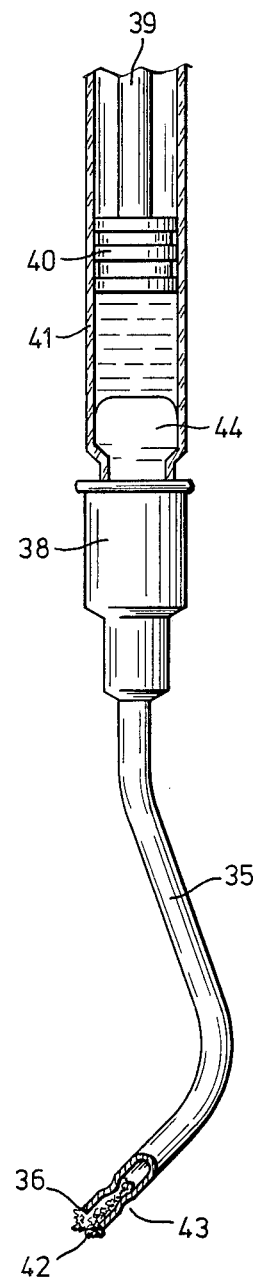
FIG. 6 is a partial sectional elevation of the preferred embodiment shown in FIG. 5.

A preferred embodiment of the invention is shown in FIGS. 5 and 6. The applicator tube 35 is of metal construction and has a curve such that the tip 36 of the tube is either on axis or slightly beyond the axis of the dispenser 37, to aid in the use of the applicator by a trained technician.

Tube 35 is attached to cap means 38 by which tube 35 is easily mounted and detached from the end of dispenser 37.

Dispenser 37 is a conventional disposable plunger-operated syringe having a plunger 39 with a plunger head 40 forming an air-tight seal with the interior of the dispenser housing 41, usually of clear plastic construction.

The tip 36 of tube 35 is provided with a small wad of porous material 42, such as a polyester filament or the like, through which the medicament can flow when pressure is applied to plunger 39. Preferably, material 42 extends only a short distance into the tip of tube 35 and may be held in position by crimping the tube 35 on both sides 43. The purpose of material 42 is to provide a burnishing action on the afflicted area, and to control the flow of medicament through tube 35. Material 42 provides some back pressure against the positive pressure of plunger 39, so as to help regulate the flow of medicament.

When the pressure is removed from the plunger 39, the back pressure of material 42 in place in the tip of tube 35 creates a slight vacuum in the form of an air bubble 44 within the applicator to prevent the further dispensing of medicament from the applicator.

It is to be understood that the particular forms of the invention described herein and illustrated in the accompanying drawings are preferred embodiments. Various changes in shape, size, materials, and arrangement of parts may be made without departing from the spirit of the invention as defined in the attached claims.

I claim:

1. An apparatus for use in applying a hemostatic agent to bleeding gingival tissue during dental procedures, comprising:
    reservoir means for holding a quantity of hemostatic agent;
    means for applying the hemostatic agent at a desired location of the gingival tissue, the proximal end of the applying means being in communication with the reservoir means such that the hemostatic agent is applied under hydraulic pressure to the desired location by the distal end of the applying means;
    porous means secured to the applying means such that a portion of the porous means extend sufficiently beyond the distal end so as to provide for at least partial sealing of the distal end of the applying means when pressed against the gingival tissue, thereby causing the hemostatic agent to be forced into said tissue by the hydraulic pressure of the applying means, and the porous means further protecting the gingival tissue from damage by the applying means as the tissue is mechanically burnished during application of the hemostatic agent; and
    means for controlled dispensing of the hemostatic agent under hydraulic pressure from the reservoir means to the distal end of the applying means.

2. An apparatus for use in applying a hemostatic agent during dental procedures as defined in claim 1, wherein the reservoir means is detachably secured to the applying means.

3. An apparatus for use in applying a hemostatic agent during dental procedures as defined in claim 2 wherein the reservoir means comprises a syringe and wherein the dispensing means comprises a plunger within the barrel of the syringe for controlling the flow of the the hemostatic agent.

4. An apparatus for use in applying a hemostatic agent during dental procedures as defined in claim 1, wherein the applying means is generally tubular in shape and is curved to facilitate placement of a hemostatic agent within a patient's mouth.

5. An apparatus for use in applying a hemostatic agent during dental procedures as defined in claim 1, wherein the porous means is secured to the applying means by positioning a portion of the porous means within the distal end of the applying means and crimping the distal end of the means so as to prevent removal of the porous means therefrom.

6. An apparatus for use in applying a hemostatic agent during dental procedures as defined in claim 1 wherein the porous means comprises a fibrous material.

7. An apparatus for use in applying a hemostatic agent during dental procedures as defined in claim 6, wherein the fibrous material is made of a polyester filament.

8. An apparatus for use in applying a hemostatic agent during dental procedures as defined in claim 1, wherein the reservoir means further comprises replaceable capsule means for containing a hemostatic agent, said capsule means being adapted to be received within the reservoir means such that it is in communication with the applying means.

9. An apparatus for use in infusing a hemostatic agent into the gingival tissue of a patient prior to taking dental impressions, the apparatus comprising:
  a reservoir for holding a quantity of hemostatic agent;
  a generally tubularly shaped member for infusing hemostatic agent into the gingival tissue of a patient, the proximal end of said tubular member being secured to and in communication with the reservoir such that the hemostatic agent is applied to the gingival tissue by the distal end of the tubular member;
  porous means secured within the distal end of the tubular member so as to substantially fill at least a portion of the interior of the tubular member thereby requiring pressure to be exerted upon the reservoir means in order for the hemostatic agent to exit from the distal end of the tubular member under hydraulic pressure, at least a portion of the porous means extending sufficiently beyond the distal end of the tubular member so as to provide for at least partial sealing of the distal end of the tubular member when pressed against the gingival tissue, thereby causing the hemostatic agent to be infused into said tissue by the hydraulic pressure of the tubular member, and the porous means further protecting the gingival tissue from injury by the tubular member as the tissue is burnished during application of the hemostatic agent; and
  means for dispensing the hemostatic agent, said dispensing means being capable of controlling the hydraulic pressure and flow of the hemostatic agent from the reservoir means through the tubular member to the porous means and infused into the gingival tissue.

10. An apparatus for use in infusing a hemostatic agent into the gingival tissue of a patient as defined in claim 9, wherein the tubular means is curved to facilitate precise application of hemostatic agent to the gingival tissue.

11. An apparatus for use in infusing a hemostatic agent into the gingival tissue of a patient as defined in claim 9, wherein the reservoir is detachably secured to the tubular member.

12. An apparatus for use in infusing a hemostatic agent into the gingival tissue of a patient as defined in claim 9, wherein the reservoir comprises a syringe and wherein the dispensing means comprises a plunger within the barrel of the syringe for controlling the flow of the hemostatic agent.

13. An apparatus for use in infusing a hemostatic agent into the gingival tissue of a patient as defined in claim 9, wherein the porous means is retained in the tubular member by crimping the distal end of the tubular member.

14. An apparatus for use in infusing a hemostatic agent into the gingival tissue of a patient as defined in claim 13, wherein the distal end of the tubular means is configured to be pressed against the gingival tissue in order to permit burnishing of such tissue.

15. An apparatus for use in infusing a hemostatic agent into the gingival tissue of a patient as defined in claim 14, wherein the porous means is a fibrous material.

16. An apparatus for use in infusing a hemostatic agent into the gingival tissue of a patient as defined in claim 15, wherein the fibrous material is a polyester filament.

17. An apparatus for use in infusing a hemostatic agent into the gingival tissue of a patient as defined in claim 9, wherein the reservoir is configured so as to receive replaceable capsules containing medicament such that the capsules are in communication with the tubular member.

* * * * *

UNITED STATES PATENT AND TRADEMARK OFFICE
CERTIFICATE OF CORRECTION

PATENT NO. : 4,578,055
DATED : March 25, 1986
INVENTOR(S) : Dan E. Fischer

It is certified that error appears in the above-identified patent and that said Letters Patent is hereby corrected as shown below:

Column 1, line 21, "and avoided" should be --and that avoided--
Column 2, line 29, "FIG. 3," should be --FIG. 3--
Column 2, lines 49-50, "shape, however, circular is preferred." should be --shape; however, a circular shape is preferred.--
Column 4, line 7, "usually of" should be --usually made of--
Column 4, line 45, "extend" should be --extends--
Column 4, line 68, "the the" should be --the--

Signed and Sealed this

Fifth Day of August 1986

[SEAL]

Attest:

DONALD J. QUIGG

Attesting Officer

Commissioner of Patents and Trademarks